US006952096B2

(12) United States Patent
Freedman (10) Patent No.: US 6,952,096 B2
(45) Date of Patent: Oct. 4, 2005

(54) METHOD AND APPARATUS FOR DETERMINING SPEED AND PROPERTIES OF FLOWING FLUIDS USING NMR MEASUREMENTS

(75) Inventor: Robert Freedman, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 119 days.

(21) Appl. No.: 10/605,069

(22) Filed: Sep. 5, 2003

(65) Prior Publication Data

US 2005/0140368 A1 Jun. 30, 2005

(51) Int. Cl.[7] .................................................. G01V 3/00
(52) U.S. Cl. ...................................... 324/303; 324/300
(58) Field of Search ................................ 324/303, 307, 324/309

(56) References Cited

U.S. PATENT DOCUMENTS

| | | | |
|---|---|---|---|
| 3,528,000 A | | 9/1970 | Schwede |
| 4,785,245 A | * | 11/1988 | Lew et al. .................... 324/308 |
| 5,291,137 A | | 3/1994 | Freedman .................... 324/303 |
| 6,046,587 A | | 4/2000 | King et al. ................... 324/306 |
| 6,111,408 A | | 8/2000 | Blades et al. ................ 324/303 |
| 6,111,409 A | | 8/2000 | Edwards et al. ............. 324/303 |
| 6,140,817 A | | 10/2000 | Flaum et al. ................. 324/303 |
| 6,229,308 B1 | | 5/2001 | Freedman .................... 324/303 |
| 6,346,813 B1 | | 2/2002 | Kleinberg .................... 324/303 |
| 6,462,541 B1 | | 10/2002 | Wang et al. .................. 324/303 |
| 6,462,542 B1 | | 10/2002 | Venkataramanan et al. . 324/303 |
| 6,479,994 B1 | * | 11/2002 | Hills et al. ................... 324/306 |
| 6,549,007 B1 | * | 4/2003 | Hills et al. ................... 324/306 |
| 6,661,226 B1 | * | 12/2003 | Hou et al. .................... 324/303 |
| 2003/0006768 A1 | | 1/2003 | Kleinberg et al. ........... 324/303 |

OTHER PUBLICATIONS

Freedman, R. et al., A New NMR Method of Fluid Characterization in Reservoir Rocks: Experimental Confirmation and Simulation Results, SPE 75325, Dec. 2001, pp. 452–464.

Bouton, J. et al., Assessment of Sample Contamination by Downhole NMR Fluid Analysis, SPE 71714, Sep. 30–Oct. 30, 2001, pp. 1–10.

Prammer, M.G. et al., The Downhole NMR Fluid Analyzer, SPWLA 42$^{nd}$ Annual Logging Symposium, Jun. 17–20, 2001, pp. 1–9.

Masak, P.C. et al., Field Test Results and Applications of the Downhole Magnetic Resonance Fluid Analyzer, SPWLA 43$^{rd}$ Annual Logging Symposium, Jun. 2–5, 2002, pp. 1–14.

Streeter, Victor L., Fluid Mechanics, 5$^{th}$ Edition, McGraw-Hill, Inc., pp. 244–250.

Abramowitz, Milton et al., Handbook of Mathematical Functions, National Bureau of Standards Applied Mathematics Series 55, Jun. 1964, pp. 887 & 916.

Hurlimann, M.D. et al, Spin Dynamics of Carr–PurcellMeiboom–Gill–like Sequences in Grossly Inhomogenous $B_0$ and $B_1$ Fields and Application to NMR Well Logging, Journal of Magnetic Resonance 143, 120–135 (2000).

* cited by examiner

Primary Examiner—Brij B. Shrivastav
(74) Attorney, Agent, or Firm—Kevin P. McEnaney; Brigitte L. Echols (57) ABSTRACT

A method for determining a property of a flowing fluid by nuclear magnetic resonance includes applying a static magnetic field to the flowing fluid; acquiring a suite of nuclear magnetic resonance measurements on the flowing fluid using a pulse sequence comprising a spoiling pulse, a wait time, and an acquisition pulse sequence, wherein the suite of nuclear magnetic measurements have different values for the wait time; and fitting the suite of nuclear magnetic resonance measurements to a forward model for responses of the flowing fluid to derive a parameter selected from a flow speed, longitudinal relaxation times of the flowing fluid, and a combination thereof.

28 Claims, 6 Drawing Sheets

METHOD AND APPARATUS FOR DETERMINING SPEED AND PROPERTIES OF FLOWING FLUIDS USING NMR MEASUREMENTS

BACKGROUND OF INVENTION

1. Field of the Invention

The invention relates generally to fluid characterization using nuclear magnetic resonance (NMR) instruments.

2. Background Art

The oil and gas industry has developed various tools capable of determining and predicting earth formation properties. Among different types of tools, nuclear magnetic resonance (NMR) instruments have proven to be invaluable. NMR instruments can be used to determine formation properties, such as the fractional volume of pore space and the fractional volume of mobile fluid filling the pore space. A general background of NMR well logging is described in U.S. Pat. No. 6,140,817.

Nuclear magnetic resonance is a phenomenon occurring in a selected group of nuclei having magnetic nuclear moments, i.e., non-zero spin quantum numbers. When these nuclei are placed in a magnetic field ($B_o$, "Zeeman field"), they each precess around the axis of the $B_o$ field with a specific frequency, the Larmor frequency ($\omega_o$), which is a characteristic property of each nuclear species and depends on the gyromagnetic ratio ($\gamma$) of the nucleus and the magnetic field strength ($B_o$) effective at the location of the nucleus, i.e., $\omega_o = \gamma B_o$.

Borehole fluid sampling and testing tools such as Schlumberger's Modular Dynamics Testing (MDT) Tool can provide important information on the type and properties of reservoir fluids in addition to providing measurements of reservoir pressure. These tools may perform measurements of the fluid properties downhole, using sensor modules on board the tools. Alternatively, these tools can withdraw fluid samples from the reservoir that can be collected in bottles and brought to the surface for analysis. The collected samples are routinely sent to fluid properties laboratories for analysis of physical properties that include, among other things, oil viscosity, gas-oil ratio, mass density or API gravity, molecular composition, $H_2S$, asphaltenes, resins, and various other impurity concentrations. However, the laboratory data may not be useful or relevant to the reservoir fluid properties because the samples may be contaminated by mud filtrate.

For example, the collected fluid samples could be emulsions of filtrate water and crude oil or, in wells drilled with oil-base muds, mixtures of reservoir crude oil and oil-base mud filtrate. In either case the contamination may render the measured laboratory data irrelevant to the actual properties of the in situ reservoir fluids. In those cases where the samples brought to the surface have low or negligible contamination, laboratory results can still be tainted (e.g., by precipitation of solids caused by temperature changes). Therefore, it is desirable that formation fluid analysis be performed, on uncontaminated samples, under downhole conditions.

Several U.S. Patents disclose methods and apparatus for making NMR measurements in a borehole on fluid samples withdrawn from earth formations. U.S. Pat. No. 6,346,813 B1 issued to Kleinberg and published U.S. Patent Application No. 2003/0006768 by Kleinberg et al. disclose an NMR module on the flowline of the MDT tool for determining different fluid properties from magnetic resonance signals. The Kleinberg patent and the Kleinberg application are assigned to the assignee of the present invention. This patent and the application are hereby incorporated by reference in their entirety. U.S. Pat. No. 6,111,408 issued to Blades et al. also discloses an NMR module that can be incorporated into a fluid sampling tool similar to the Schlumberger MDT™ tool. The NMR module can perform different NMR measurements including $T_1$ (longitudinal relaxation time), $T_2$ (transverse relaxation time), and D (diffusion constant). U.S. Pat. No. 6,111,409 issued to Edwards et al. discloses an apparatus and method for measuring spin-echo signals from carbon-13 nuclei and a spectral method of analyzing these measurements to determine the ratio of aliphatic to aromatic hydrocarbons from the chemical shift spectrum. U.S. Pat. No. 3,528,000 issued to Schwede discloses different methods, including those using an open hole packer, for withdrawing fluid samples into a borehole tool in order to perform NMR measurements on the fluid samples. However, none of these prior art patents disclose methods for determining flow speed or $T_1$ of flowing fluids.

U.S. Pat. No. 6,046,587 issued to King and Santos discloses methods and apparatus for measuring flow speed of multiphase fluids flowing in a pipeline. The King and Santos patent teaches using the ratio of NMR free-induction decay (FID) amplitudes of signals acquired with different delay times to infer flow speed using a single NMR sensor. However, the FID signal is difficult to measure using permanent magnets because static magnetic field variations will result in signals that decay too fast for reliable detection. Moreover, the King and Santos methods for determining flow speed do not account for the fact that there is a distribution of flow speeds in a pipe. In another embodiment, the King and Santos apparatus consists of two separated NMR sensors. The flow speed and fluid volumes for multiphase fluid flow are computed from FID measurements in the two sensors. However, the computation requires prior knowledge of the fluid $T_1$ distributions.

Two methods for measuring the speed of fluids flowing through a flowline of a fluid sampling tool are described in a U.S. patent application Ser. No. 10/349011, filed by Madio et al. on Jan. 22, 2003. This application is assigned to the assignee of the present invention and is hereby incorporated by reference in its entirety. Both methods require that the static magnetic field of the NMR apparatus have a gradient in the direction of the flow. The first method exploits the fact there is a Larmor frequency shift between different wait time measurements in a variable wait time pulse sequence. The measured frequency shifts are proportional to both the flow speed and the gradient. The second method is based on the fact that the measured phase difference between odd and even echoes is proportional to both the average flow speed and the gradient.

While these prior art methods are useful for determining formation fluid properties, there remains a need for better methods for measuring a property of a fluid flowing in a formation testing tool using NMR instruments.

SUMMARY OF INVENTION

In one aspect, embodiments of the invention relate to methods for determining a property of a flowing fluid by nuclear magnetic resonance. A method for determining a property of a flowing fluid by nuclear magnetic resonance in accordance with one embodiment of the invention includes applying a static magnetic field to the flowing fluid; acquiring a suite of nuclear magnetic resonance measurements on the flowing fluid using a pulse sequence comprising a spoiling pulse, a wait time, and an acquisition pulse sequence, wherein the suite of nuclear magnetic measurements have different values for the wait time; and fitting the suite of nuclear magnetic resonance measurements to a forward model for responses of the flowing fluid to derive a parameter selected from a flow speed, longitudinal relaxation times of the flowing fluid, and a combination thereof.

Another aspect of the invention relates to methods for monitoring contamination in a flowing fluid being withdrawn into a formation fluid testing tool using nuclear magnetic resonance. A method for monitoring contamination in a flowing fluid being withdrawn into a formation fluid testing tool using nuclear magnetic resonance in accordance with one embodiment of the invention includes applying a static magnetic field to the flowing fluid; acquiring a suite of nuclear magnetic resonance measurements of the flowing fluid using a pulse sequence comprising a spoiling pulse, a wait time, and an acquisition pulse sequence, wherein the suite of nuclear magnetic measurements have different values for the wait time; fitting the suite of nuclear magnetic resonance measurements to a forward model for responses of the flowing fluid to derive a property of the flowing fluid; and monitoring a level of contamination in the flowing fluid based on the derived property of the flowing fluid.

Another aspect of the invention relates to an NMR instrument for measuring a property of a flowing fluid. A nuclear magnetic resonance apparatus in accordance with one embodiment of the invention includes a flow pipe including a prepolarization section and an investigation section, wherein the prepolarization section is upstream of the investigation section; a magnet disposed around the flow pipe for creating a static magnetic field covering the prepolarization section and the investigation section; an antenna disposed around the flow pipe at the investigation section for generating an oscillating magnetic field having a magnetic dipole substantially perpendicular to a magnetic dipole of the static magnetic field, and for receiving a nuclear magnetic resonance signal; and a circuitry for controlling generation of the oscillating magnetic field and reception of the nuclear magnetic resonance signal by the antenna.

Other aspects of the invention will become apparent from the following description, the drawings, and the claims.

DETAILED DESCRIPTION

Embodiments of the invention relate to methods and apparatus for determining speeds and properties of flowing fluids using NMR measurements. The methods disclosed herein for determining flow speed do not depend on static magnetic field gradients.

Some embodiments of the invention also relate to methods for measuring longitudinal relaxation time ($T_1$) of the fluid. The measurement of $T_1$ provides a means for monitoring contamination levels in the reservoir fluids that are being withdrawn from the reservoir into a borehole fluid testing/sampling tool, such as the Modular Dynamics Tester tool sold under the trade name of MDT™ by Schlumberger Technology Corporation (Houston, Tex.) or any similar fluid sampling tool. Monitoring changes in $T_1$ with time is useful for determining when to divert or stop the flow in order to: (1) to make in situ NMR measurements of longitudinal ($T_1$) or transverse relaxation times ($T_2$), diffusion coefficients (D), or chemical shift spectra, or (2) collect a fluid sample that can be brought to the surface and sent to a laboratory for analysis.

Some embodiments of the invention relate to methods for computing the viscosities of the flowing fluids. In accordance with one embodiment of the invention, the $T_1$ of the fluid can also be used to estimate reservoir oil viscosity using known empirical correlations, provided that the gas-oil ratio of the fluid is known from other measurements. Another method in accordance with the invention may use measurements of pressure differential ($\Delta P$) across the flowline together with the flow speed, e.g., determined by NMR, to compute the viscosity.

Methods of the invention may be practiced with an NMR instrument modified from those known in the art. The NMR instrument may be in the laboratory or be part of a wireline tool, such as a formation tester (fluid sampling tool) used to analyze the fluids withdrawn from the formations.

Figure 1:
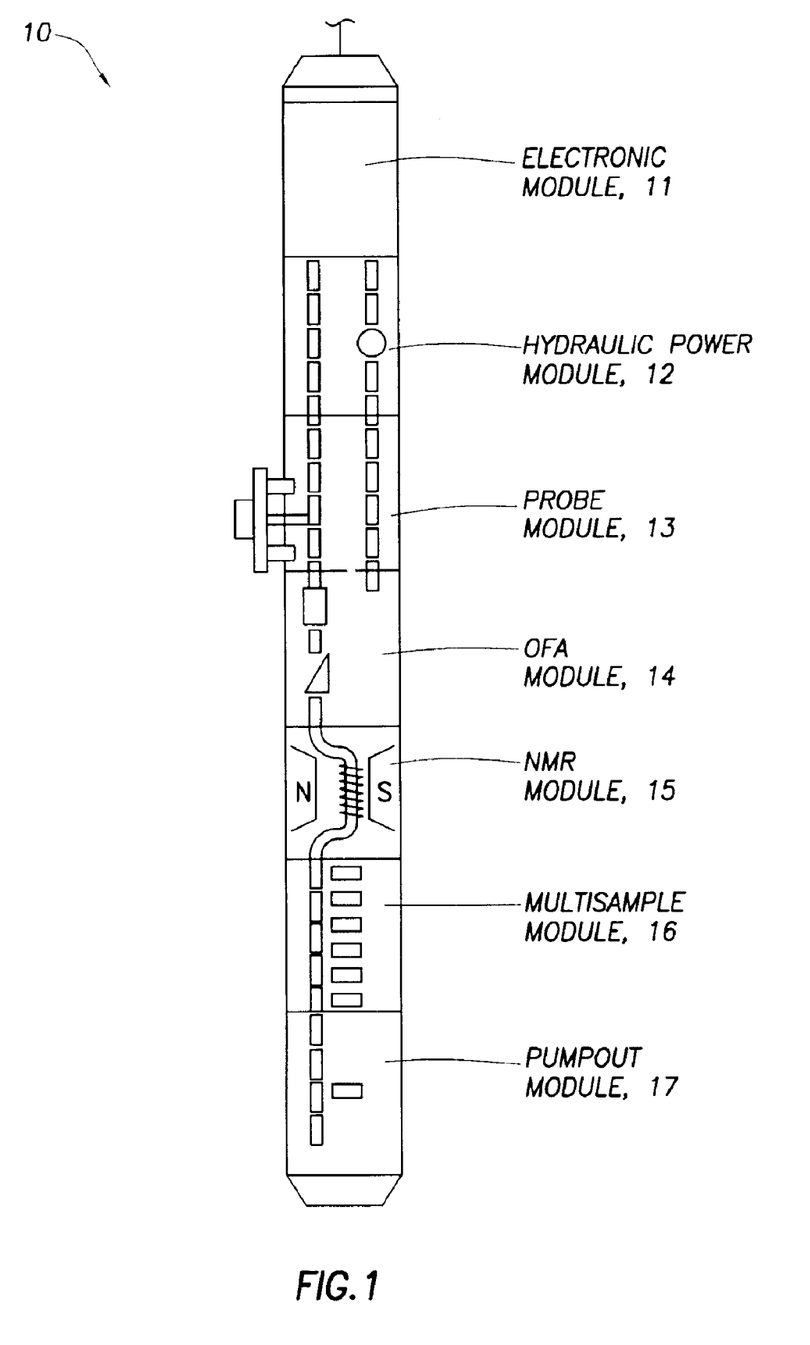
FIG. 1 shows a formation fluid testing tool including an NMR module suitable for practicing embodiments of the invention.

FIG. 1 illustrates a formation fluid testing/sampling tool, such as Schlumberger's Modular Dynamics Testing Tool (MDT), which comprises several parts which enable extraction of fluids from permeable earth formations. As shown, the formation fluid testing tool 10 includes the following modules: an electronic module 11, which may include a processor and a memory; a hydraulic power module 12; a probe module 13, which may be deployed to make a hydraulic seal with the formation; a pumpout module 17; an optical fluid analyzer (OFA) 14; and a multisample module 16. In addition, the formation fluid testing tool 10 includes an NMR sensor 15.

An NMR sensor 15 in accordance with an embodiment of the invention includes (1) a magnet (e.g., a permanent magnet) that is designed to produce a static magnetic field in the flowline (flow pipe) of the formation fluid testing tool 10, and (2) an RF antenna (which may function as a transmitter and a receiver) designed to radiate a oscillating magnetic field having its magnetic dipole substantially perpendicular (orthogonal) to that of the static magnetic field. The frequency of the oscillating magnetic field is selected to be equal to the Larmor frequency of the NMR sensitive nuclei (e.g., $^1$H or $^{13}$C) under investigation. Because of signal-to-noise considerations, it is preferred to measure $^1$H nuclei in rapidly flowing fluids. For stationary measurements (i.e., when fluid is not flowing), signals from other nuclei, including $^{13}$C may be measured. One of ordinary skill in the art would appreciate that the same RF antenna may function as a transmitter to transmit the oscillating magnetic field and as a receiver to receive the signals, as disclosed in U.S. Pat. No. 6,346,813 B1 issued to Kleinberg. Alternatively, separate transmitter and receiving antennas may be used. The magnet may have a prepolarization region for polarizing the fluid before it enters the transmitter/receiver antenna region. The pre-polarization may be necessary for obtaining measurable signals from rapidly moving nuclei.

Figure 2A:
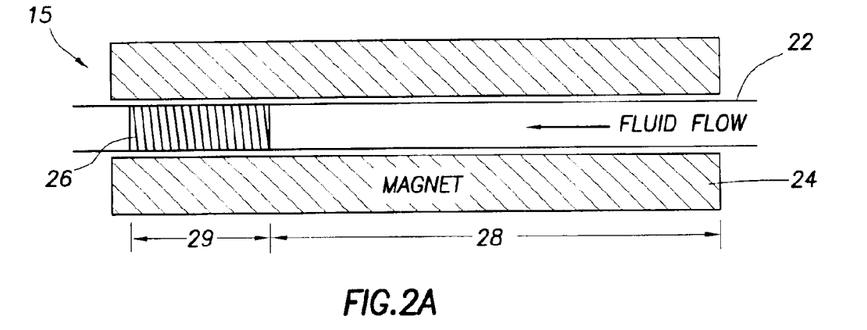
FIG. 2A shows a schematic of an NMR sensor in accordance with one embodiment of the invention.

FIG. 2A shows an illustration of an NMR sensor 15 in accordance with one embodiment of the invention for determining flow speed and other properties of a fluid flowing in a flowline 22. As shown, the sensor 15 includes a non-conductive and non-magnetic flowline 22, a permanent magnet 24, and an antenna 26 for transmitting and receiving radio frequency (RF) signals.

As shown, the flowline (flow pipe) 22 includes a prepolarization section 28 that is upstream of an investigation section 29. The magnet 24 is disposed around both the prepolarization section 28 and the investigation section 29. The magnet 24 may be a permanent magnet or an electromagnet magnet. As shown, the flowline 22 is made of a non-conductive and non-magnetic material, such as a composite or polymer material. If the flowline 22 is made of a conductive or magnetic material (e.g., steel), then the antenna 26 is preferably located inside the flowline.

For the sensor shown in FIG. 2A, the antenna (solenoid coil) 26 functions as both a transmitter and a receiver. Alternatively, the NMR sensor 15 may include two antennas: one functions as a transmitter and the other as a receiver. Furthermore, the antenna may comprise a solenoid coil, a loop, or a saddle coil. The antenna 26 substantially covers the investigation section 29 of the flowline 22.

The NMR measurements according to methods of the invention includes a suite of variable wait time (W) measurements. Prior to each wait time (W), the magnetization is first spoiled by pulses designed to "kill" the magnetization so that $M_x=M_y=M_z=0$. Following the spoiling pulse and the wait time, a 90-degree pulse followed by a 180-degree pulse (e.g., a spin-echo pulse) is applied to the transmitter to generate a spin echo.

The receiving antenna measures the in-phase and quadrature components of the spin-echo signal. The measurement is repeated for a number of different wait times. In other embodiments of this invention, multiple 180-degree pulses may be applied to produce multiple spin-echo signals. In addition, one of ordinary skill in the art would appreciate that spin-echoes may also be obtained using pulses other than 90- and 180-degree pulses, for example, using composite pulses.

The amplitudes of the detected spin-echo signals for the different wait times depend on flow speed, wait time, receiver and transmitter lengths, magnet pre-polarization length, and the $T_1$ distribution of the fluid. All of these parameters, except the flow speed and the $T_1$ distribution of the fluid, are either fixed by the sensor design or by the pulse sequence. If sufficient sets of measurements are available, these parameters may be derived by fitting the measured signals to a proper model that simulates the NMR response of the flowing fluid. That is, the data may be interpreted by forward modeling.

The method disclosed below employs a theoretical forward model that allows the computation of the detected echo signals for any combination of the aforementioned pulse sequence, sensor parameters, flow speed, and $T_1$ distribution. The forward model may be fit, by inversion, to the measured echo signals to determine the apparent flow speed and $T_1$ distribution. Alternatively, if the flow speed is known from other measurements then the forward model can be fit by inversion to determine the $T_1$ distribution.

Sensor and Variable Wait Time Pulse Sequence

Figure 2B:
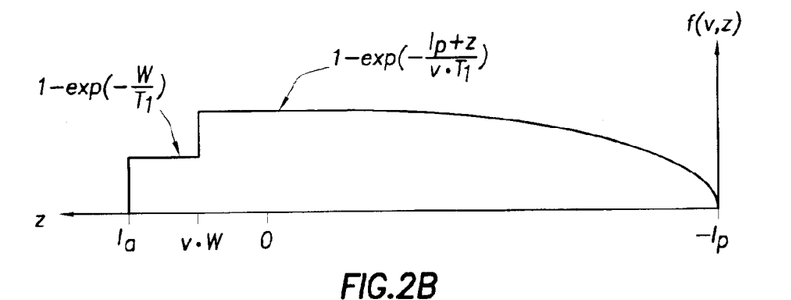
FIG. 2B shows a schematic of spin polarization profile along a flow pipe of an NMR sensor in accordance with one embodiment of the invention.

FIG. 2B shows that the speed and position dependent polarization profile ($f(v,z)$) over the length ($l_a$) of the receiver coil (shown as 26 in FIG. 2A) is made up of two parts—one part comes from fresh spins that are "pre-polarized" as they travel in the static magnetic field into the receiver during the wait time (W) and the second part that comes from spins that were in the receiver coil and are "re-polarized" during the wait time (W). The pre-polarization length ($l_p$) shown in FIGS. 2A and 2B corresponds to the length of the prepolarization region 28.

The position and speed dependent polarization function is given by the equation, $$f(v, z) = 1 - \exp\left(-\frac{T(z, v)}{T_1}\right). \tag{1}$$

where $T(z,v)$ is the polarization time for a spin with position z and speed v, and $T_1$ is the longitudinal relaxation time of the spins. The polarization time, $T(z,v)$, is defined as:

$$T(z, v) = \frac{l_p + z}{v} \text{ for } 0 \leq z \leq v \cdot W \tag{2a}$$

and, $$T(z,v) = W \text{ for } v \cdot W < z \leq l_a, \tag{2b}$$

It is clear from the above equations that the speed (v) and position (z) dependent polarization function, $f(v,z)$, also depends on $l_p$, W, and $T_1$. However, these dependencies are implicit in Eq. 1 because polarization time, $T(z, v)$, is used to simplify the notation. These equations can be more easily understood following a discussion of the variable wait time (VWT) pulse sequence shown in FIGS. 3A and 3B.

Figure 3A:
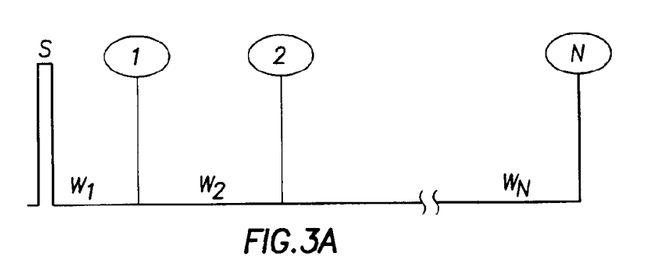
FIG. 3A shows a diagram of a pulse sequence for acquiring variable wait time NMR measurements according to one embodiment of the invention.

FIG. 3A shows a suite of variable wait time pulses consisting of N measurements. N is preferably on the order of 10. After each measurement in the suite, one or more spoiling pulses (collectively denoted by the pulse S) are applied to destroy any remnant magnetization before starting the wait time for the next measurement. The duration and frequencies of the spoiling pulses are instrument dependent and can be determined empirically.

Figure 3B:
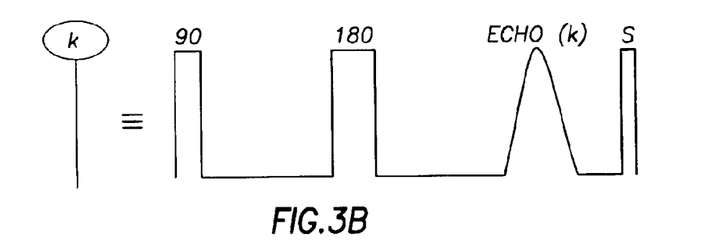
FIG. 3B shows a diagram of a pulse sequence including a spoiling pulse according to one embodiment of the invention.

As shown schematically by the "tadpole" in FIG. 3B, following each wait time a 90-degree excitation pulse is applied to rotate the longitudinal magnetization onto the transverse plane. The signal from the transverse magnetization rapidly dephases due to inhomogeneity (or other factors) in the static magnetic field, but is refocused by the 180-degree pulse to produce a spin-echo. After the spin-echo signals are acquired, a spoiling pulse is applied to remove the magnetization of the spins within the receiver coil (shown as 26 in FIG. 2A). Those skilled in the art will recognize that a variable wait time sequence like the one shown in FIG. 3 can also be used observe the free-induction decay signals instead of a spin echo. That is, the 180-degree pulse shown in FIG. 3B can be omitted and the free-induction decay signal can be observed following the 90-degree pulse. Only minor and obvious modifications to the forward model are required. Those skilled in the art will also recognize that other $T_1$-sensitive sequences, such as inversion recovery or saturation recovery pulse sequences, could also be employed with obvious modifications to the forward model. Both the inversion-recovery and the saturation-recovery pulse sequences are generally referred to as "$T_1$-relaxation investigation pulse sequences" in this description.

The pulse sequence used to acquire the NMR signals (FID or echoes) are generally referred to as an "acquisition pulse sequence" in this description. An acquisition pulse sequence may include a single 90-degree pulse, a spin-echo pulse (i.e., a 90-degree pulse followed by a 180-degree pulse), and the variants of the spin-echo pulse that include multiple 180-degree (refocusing) pulses following the 90-degree pulse (e.g., a CPMG). Thus, the "variable wait time pulse sequence" as shown in FIGS. 3A and 3B comprises a spoiling pulse, a wait time, and an acquisition pulse sequence. The spin-echo pulse sequence and its variant (e.g., CPMG) are generally referred to as a "spin-echo pulse sequence" in this description. That is, a "spin-echo pulse sequence" not only comprises a single 90-degree pulse and a single 180-degree (refocusing) pulse, but also comprises multiple 180-degree (refocusing) pulses after the 90-degree pulse.

During each wait time, fresh or pre-polarized spins move into the antenna region. Eq. 2a shows that in the region, $0 \leq z \leq vW$, fresh spins have entered the antenna during the wait time. The length of this region depends on both the flow speed (v) and the wait time (W), i.e., it depends on the product of the flow speed (v) and the wait time (W). The polarization time for these fresh spins is independent of the wait time. Instead, it depends on the duration that the spins have been exposed to the static magnetic field since they entered the permanent magnet. This is because this portion of the fluid was outside the transmitter/receiver antenna (shown as 26 in FIG. 2A) when the spoiling pulse is applied and the magnetizations of the spins in this portion of the fluid were not "killed" by the spoiling pulse. On the other hand, as can be seen from Eq. 2b, the re-polarization of the spins in the adjoining region of length, $l_a - vW$, is controlled by the wait time (W) because these spins were in the transmitter/receiver region when the spoiling pulse was applied. The magnetizations of these spins were removed by the spoiling pulse, and any polarization detected by the receiver is due to repolarization during the wait time (W). If the wait time is long or the flowing speed is fast enough such that the product, vW, exceeds the antenna length, then only fresh spins (those that enter the receiver antenna after the spoiling pulse) are measured and the polarization function is independent of W Derivation of the NMR Forward Model for Flowing Fluids The methods disclosed herein preferably employ forward models for predicting the responses of the NMR sensor for a fluid with a given flow speed and distribution of $T_1$ relaxation times. The response of the sensor also depends on the wait times and physical parameters of the sensor such as the antenna length, the magnet pre-polarization length, and the radius of the flowline. For a given wait time and sensor design the only variables in the forward model arc the flow speed and the $T_1$ distribution of the fluid. The flow speed and $T_1$ distribution are preferably determined by inversion of a forward model. The forward model is derived in the following paragraphs.

Figure 4A:
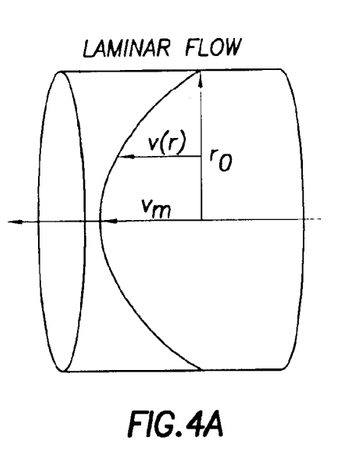
FIGS. 4A and 4B show a schematic diagram illustrating a laminar flow and a non-laminar flow, respectively.
Figure 4B:
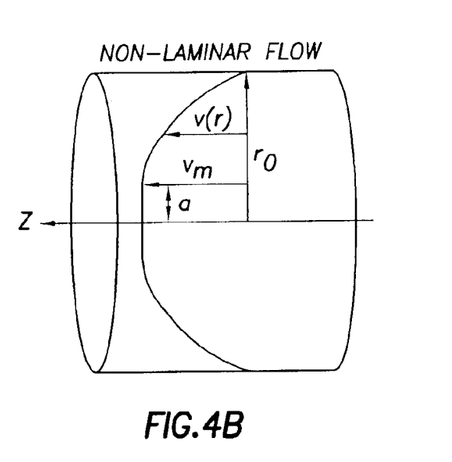

To accurately model the NMR responses of flowing fluids, the fact that the velocity profile of a laminar flow for a viscous fluid flowing in a pipe is parabolic should be taken into account. See e.g., Victor L. Streeter, "*Fluid Mechanics,*" McGraw-Hill Book Co., $5^{th}$ Edition. p. 244. In a laminar flow, the maximum flow velocity, $v_{mo}$ occurs at the axis of the pipe, while the velocity is zero at the wall of the pipe. The laminar flow regime in circular pipes is characterized by the values of Reynolds number, $R \leq 2000$~$3000$, where the exact upper limit for laminar flow depends on the surface roughness of the pipe. The Reynolds number is defined by, $$R = \frac{2r_o v \rho}{\eta}, \qquad (3)$$

where $r_o$ is the radius of the flowline pipe), v is the average flow speed, $\rho$ is the fluid mass density, and $\eta$ is the viscosity of the fluid. In contrast to a laminar flow, turbulent flow has a chaotic component and is much more difficult to model. One feature of turbulent flow is a flattening of the velocity parabolic profile. FIG. 4 shows the velocity profiles for laminar flow (A) and non-laminar flow (B) in a circular pipe.

To develop a forward model, an expression for the echo amplitudes measured by the variable wait time pulse sequence shown in FIGS. 3A and 3B is needed. If $A_i$ represents the amplitude of a phase-corrected echo signal measured with a wait time $W_i$, then $A_i$ can be written in the form of a volume integral over the sensitive volume ($\Omega$) of the receiver antenna, i.e., $$A_i = \int_\Omega S_a(\vec{r}) \{ \int P(T_1) f(v(r), z, T_1, l_p, W_i) dT_1 \} d^3 r. \qquad (4)$$

The inner integral in Eq. 4 is a $T_1$-weighted integral over a speed and position dependent polarization function. The weighting function is the $T_1$ distribution of the fluid, $P(T_1)$. The volume integral is weighted by the spatial sensitivity function, $S_a(r)$, that can be determined by measurements or calculations. To simplify the following discussion, it is useful to consider a receiver having a uniform spatial sensitivity so that, $$S_a = \frac{1}{\Omega} = \frac{l}{\pi r_o^2 l_a} \qquad (5)$$

where $r_o$ is the radius of the flow pipe. Using Eq. 5 and cylindrical coordinates $(r, \theta, z)$, the integral in Eq. 4 can be written in the following form:

$$A_i = \frac{2}{l_a r_o^2} \int_0^\infty P(T_1) \left\{ \int_0^{r_o} \left[ \int_0^{l_a} f(v(r), z, T_1, l_p, W_i) dz \right] r dr \right\} dT_1. \qquad (6)$$

In arriving at Eq. 6, the angular integral was performed assuming the sensitivity function has azimuthal symmetry. Note that the polarization function in the integrand of Eq. 6 is given by Eqs. 1 and 2a–2b. To proceed with the evaluation of $A_i$, the speed dependent polarization function may be obtained by integrating over the z co-ordinate, i.e., $$f(v(r), T_1, l_p, l_a, W_i) = \quad (7)$$

$$\int_0^{W_i \cdot v} \left(1 - \exp\left(-\frac{(l_p + z)}{v \cdot T_1}\right)\right) \frac{dz}{l_a} + \int_{W_i \cdot v}^{l_a} \left(1 - \exp\left(-\frac{W_i}{T_1}\right)\right) \frac{dz}{l_a}.$$

The above integrals can be performed analytically to produce:

$$f(v(r), T_1, l_p, l_a, W_i) = \frac{W_i \cdot v}{l_a} - \frac{v \cdot T_1}{l_a}\left(1 - \exp\left(-\frac{W_i}{T_1}\right)\right) \cdot \exp\left(-\frac{l_p}{v \cdot T_1}\right) + \quad (8a)$$

$$\left(1 - \exp\left(-\frac{W_i}{T_i}\right)\right) \cdot \left(\frac{l_a - W_i \cdot v}{l_a}\right)$$

for $W_i \cdot v < l_a$, and for $W_i \cdot v \geq l_a$, the integral is given by:

$$f(v(r), T_1, l_p, l_a, W_i) = 1 - \frac{v \cdot T_1}{l_a}\left(1 - \exp\left(-\frac{l_a}{v \cdot T_1}\right)\right) \cdot \exp\left(-\frac{l_p}{v \cdot T_1}\right). \quad (8b)$$

Before proceeding further, it is useful to make some observations in order to provide some insights into Eqs. 8a–8b. The first two terms in Eq. 8a account for the pre-polarization of the spins, whereas the last term is due to re-polarization of spins that are not removed by outflow from the receiver antenna region during the wait time (W). Note that Eq. 8b can be obtained from 8a by setting $W_i \cdot v = l_a$. Once the condition $W_i \cdot v \geq l_a$ is met, the sensitive region is totally filled with fresh spins and the polarization function is independent of $W_i$.

The functions in Eqs. 8a and 8b represent the radial sensitivity functions after integration over the z co-ordinate. Next, it is necessary to integrate these functions over the radial co-ordinate. The radial dependence of the radial sensitivity function arises from the radial variations of the flow speed in the flowline (see FIG. 4). For laminar flow the velocity profile is parabolic and can be written in the form, $$v(r) = -\frac{(r^2 - r_o^2)}{r_o^2} v_m \quad (9)$$

where $r_o$ is the radius of the flowline and $v_m$ is the maximum flow speed on the axis of the flowline (i.e., at r=0) as shown in FIG. 4. It follows from Eq. 9 that the average flow speed with a laminar flow is $v_m/2$. While Eq. 9 describes a commonly used model for laminar flow, an alternative laminar flow model may be described as follows:

$$v(r) = v_m\left(1 - \frac{r}{r_o}\right)^{\frac{1}{n}} \quad (9a)$$

where n is typically between 5 and 10. Embodiments of the invention can use either of these two laminar flow models or any variation thereof. For clarity, the following description is based on the model described in Eq. 9. However, one of ordinary skill in the art would appreciate that the model described in Eq. 9a can substitute for the model of Eq. 9 in the following description.

Consider the following integral over the radial coordinate, $$F(v_m, T_1, l_p, l_a, W_i) = \frac{2}{r_o^2}\int_0^{r_o} rf(v(r), T_1, l_p, l_a, W_i)dr \quad (10)$$

Because Eq. 9 describes the relationship between the radius r and the flow speeds v, the integral over the radius r shown in Eq. 10 can be transformed into an integral over flow speeds v by using Eq. 9 to make a change of variables, e.g., $$dv = -\frac{2r}{r_o^2} v_m dr. \quad (11)$$

Eqs. 9 and 11 may be used to change the integration variable and limits in Eq. 10 to give, $$F(v_m, T_1, l_p, l_a, W_i) = \int_0^{v_m} f(v, T_1, l_p, l_a, W_i)\frac{dv}{v_m}. \quad (12)$$

It is useful to make another change of variables in the integral in Eq. 12. Making the change of variables $v = v_m \cdot \xi$ in the integral in Eq. 12 leads to the integral, $$F(v_m, T_1, l_p, l_a, W_i) = \int_0^1 f(v_m \xi, T_1, l_p, l_a, W_i)d\xi, \quad (13)$$

which is in a form that can be accurately performed numerically using the Gaussian integration method. Assembling the pieces, Eq. 6 for the echo amplitudes can be rewritten in the following form:

$$A_i = \int_0^\infty P(T_1)F(v_m, T_1, l_p, l_a, W_i)dt_1. \quad (14)$$

Note that with known values of $l_p$, $l_a$, and $W_i$, the model echo amplitudes depend only on $P(T_1)$, the $T_1$ distribution, and the maximum flow speed, $v_m$. As described in a later section, estimates of $P(T_1)$ and $v_m$ may be obtained by using suites of variable wait time data to invert the model. For laminar flow, $v_m$ and the flowline radius $r_o$ completely specify the velocity profile in Eq. 9.

The expression in Eq. 13 was derived based on the parabolic velocity fluid profile described in Eq. 9. This is appropriate for laminar flow. However, for non-laminar profile shown in FIG. 4, the equation derived in Eq. 13 is not valid and should be modified.

The velocity profile for the non-laminar flow depicted in FIG. 4 can be described by the following equations:

$$v(r) = v_m \text{ for } 0 \leq r \leq a, \quad (15a)$$

and, $$v(r) = -\frac{\{(r-a)^2 - (r_o - a)^2\}v_m}{(r_o - a)^2} \text{ for } a \leq r \leq r_o. \quad (15b)$$

Using Eqs. 15a and 15b, the integral in Eq. 10 can be expressed as the sum of two integrals, i.e., $$F(v_m, T_1, l_p, l_a, W_i) = \quad (16)$$

$$\frac{2}{r_o^2}\int_0^a rf(v_m, T_1, l_p, l_a, W_i)dr + \frac{2}{r_o^2}\int_a^{r_o} rf(v(r), T_1, l_p, l_a, W_i)dr.$$

The first integral on the right is straightforward. Transforming the integration over r to integration over v by using Eq. 15b performs the second integral. The last step is to introduce the change of variables $v=v_m \cdot \xi$ to convert Eq. 16 into the following form:

$$F(v_m, a, T_1, l_p, l_a, W_i) = \frac{a^2}{r_o^2} f(v_m, T_1, l_p, l_a, W_i) + \frac{(r_o-a)^2}{r_o^2} \int_o^1 f(v_m \cdot \xi, T_1, l_p, l_a, W_i) d\xi. \quad (17)$$

Note that if a=0, Eq. 17 reduces to Eq. 13 for laminar flow. Moreover, the model echo amplitudes in Eq. 14 now depend on the parameter a in addition to their dependence on $v_m$ and $P(T_1)$. By inversion of the forward model, it is feasible to estimate the parameter, a, and, therefore, to infer the onset or existence of turbulent or non-laminar flow.

Numerical Integration

The integral in Eq. 17 can be expressed as a weighted sum of the integrand over a set of fixed abscissas, i.e., $$F(v_m, a, T_1, l_p, l_a, W_i) = \frac{a^2}{r_o^2} f(v_m, T_1, l_p, l_a, W_i) + \frac{(r_o-a)^2}{2r_o^2} \sum_{k=1}^{n} w_k f(v_m \cdot \xi_k, T_1, l_p, l_a, W_i). \quad (18)$$

The weights, $w_k$, and the abscissas, $x_k$, for nth-order Gaussian integration can be found in tables given in "Handbook of Mathematical Functions With Formulas, Graphs, and Mathematical Tables," edited by M. Abramowitz and L. A. Stegun, National Bureau of Standards Applied Mathematics Series 55, June 1964. For example, in the table below the abscissas and weights for 6th order Gaussian integration are shown.

| Abscissas and Weights for 6th Order Gaussian Integration | |
| --- | --- |
| $\pm x_k$ | $w_k$ |
| 0.238619186083197 | 0.467913934572691 |
| 0.661209386466265 | 0.360761573048139 |
| 0.932469514203152 | 0.171324492379170 |

The abscissas given in the table are for integrals in the range from (−1,1). The abscissas in Eq. 18 can be obtained from the latter using the equation, $$\xi_k = \frac{x_k+1}{2}. \quad (19)$$

In performing the summation in Eq. 18, it is useful to recall that the "integrand" is the speed dependent polarization function in Eqs. 8a or 8b depending on whether $\xi_k < l_a/v_m W_i$ or $\xi_k \geq l_a/v_m W_i$.

Inversion of the Forward Model

Once the NMR data of the flowing fluid are acquired with variable wait times, they are fitted to the forward model to provide the flow speed and $T_1$ information of the flowing fluid in accordance with embodiments of the invention. The inversion involves varying the parameters $v_m$, $P(T_1)$, and a in the forward model until the measured echo amplitudes fit the ones predicted by the model. There are many different ways of fitting the measured data to the model. The following describes two approaches as examples. One of ordinary skill in the art would appreciate that other approaches may also be used without departing from the scope of the invention.

Inversion Method No. 1

Measured NMR data consist of signals measured in the in-phase and quadrature channels of an NMR instrument. The quadrature signals are ninety degrees out of phase with respect to the corresponding signals detected in the in-phase channel.

The measured signals include noises. Thus, to fit the model to the measurement data, some measurement noises should be added to the signals derived from the model. The following equations illustrate this approach:

$$\tilde{A}_{i,r} = A_i \cos \phi + I_{i,r}, \quad (20a)$$

$$\tilde{A}_{i,q} = A_i \sin \phi + I_{i,q}, \quad (20b)$$

where $\tilde{A}_{i,r}$ and $\tilde{A}_{i,q}$ are measured amplitudes in the in-phase and the quadrature channels, respectively, for the measurement with wait time, $W_i$; $A_i$ is the model predicted signal amplitude; $\phi$ is the model predicted signal phase; and $I_{i,r}$ and $I_{i,q}$, are noises in the signal and quadrature channels, respectively. $I_{i,r}$ and $I_{i,q}$, are assumed to be zero-mean Gaussian noises with equal variances, $\sigma^2$, in the two channels. Using Eq. 14, the signal amplitude $A_i$ can be written in the following form:

$$A_i = \sum_{i=1}^{N_c} a_i F_{i,1}(v_m, a), \quad (21)$$

where the integral over $T_1$ in Eq. 14 has been replaced by a summation over the $N_c$ amplitudes ($a_1$) that are used to approximate the $T_1$ distribution. The following quantities are defined:

$$F_{i,j}(v_m, a) \equiv F(v_m, a, T_{1,l}, l_a, l_p, W_i). \quad (22)$$

and recalled from Eq. 18 that includes the parameter, a, to describe the radius over which the parabolic front is flattened out because of the non-laminar flow.

The discrete set of relaxation times, $T_{1,l}$, are fixed and can be selected to be equally spaced on a logarithmic scale. Because the in-phase and the quadrature signals are 90 degrees out of phase to each other, the signal phase, $\phi$, may be estimated from the measured in-phase and quadrature amplitudes using the following equation:

$$\hat{\phi} = \arctan\left(\frac{\sum_{i=1}^{N_m} \tilde{A}_{i,q}}{\sum_{i=1}^{N_m} \tilde{A}_{i,r}}\right). \quad (23)$$

where the caret over $\phi$ denotes the fact that it is an estimate; and $N_m$ is the number of measurements (different wait times) in the variable wait time measurement suite.

The phase estimate obtained from Eq. 23 may then be used to compute the phase-corrected signal plus noise amplitudes and the root mean square (rms) noise according to the method disclosed in U.S. Pat. No. 5,291,137 issued to Freedman ("the Freedman patent"). This patent is incorporated by reference in its entirety. Briefly, $$\tilde{A}_i^{(+)} = \tilde{A}_{i,r} \cos \hat{\phi} + \tilde{A}_{i,q} \sin \hat{\phi} \quad (24a)$$

and, $$\tilde{A}_i^{(-)} = \tilde{A}_{i,r} \sin \hat{\phi} - \tilde{A}_{i,q} \cos \hat{\phi}. \quad (24b)$$

The Freedman patent shows that, $$\langle \tilde{A}_i^{(+)} \rangle = A_i \tag{25}$$

where the angular bracket denotes the expectation value and $A_i$ is the model predicted amplitude as described in Eq. 14. The rms noise estimate can be computed from the equation, $$\hat{\sigma} = \sqrt{\frac{1}{N_m} \sum_{i=1}^{N_m} (\tilde{A}_i^{(-)})^2}. \tag{26}$$

The measured amplitude data may be fit to the model amplitudes by minimizing the sum of the squared fit errors, for example, by minimizing an objective function:

$$E(v_m, a, \{a_i\}) = \sum_{i=1}^{N_m} (\tilde{A}_i^{(+)} - A_i(v_m, a, \{a_i\}))^2 + \gamma \sum_{i=1}^{N_m} a_i^2, \tag{27}$$

with respect to the parameters $v_m$, $a$, and the set of amplitudes $a_1$. The last term in Eq. 27 is used to stabilize the solution by reducing the effects of noise amplification that can occur in under determined inverse problems. The parameter $\gamma$ is a regularization parameter and $\gamma \geq 0$.

Note that "spin-dynamics" effects in the magnetic field gradient of a permanent magnet can lead to an attenuation of the measured echo amplitudes. See Hürlimann and Griffin, "*Spin-Dynamics of Carr-Purcell-Meiboom-Gill-like Sequences in Grossly Inhomogeneous $B_0$ and $B_1$ Fields and Application to NMR Well Logging,*" J. Magn. Reson. v. 143, 120–135 (2000). Therefore, the echo amplitudes in Eq. 27 are corrected for spin-dynamics attenuation.

The minimization in Eq. 27 can be performed using a number of commercially available optimization programs that can minimize linear or non-linear functions subject to constraints. One such program is the double precision subroutine called "DLCONG" that is available as part of a library of optimization codes sold under the trade name of IMSL™ by the Visual Numerics Corp. (San Ramon, Calif.). The DLCONG code is more robust if analytical functions can be provided for the partial derivatives of the objective function. The derivatives for the objective function can be computed analytically. For example, from Eq. 27, the following derivatives may be obtained, $$\frac{\partial E}{\partial a_k} = -2 \cdot \sum_{i=1}^{N_m} (\tilde{A}_i^{(+)} - A_i(v_m, a, \{a_i\})) F_{i,k}(v_m, a) + 2 \cdot \gamma \cdot a_k, \tag{28}$$

and, $$\frac{\partial E}{\partial v_m} = -2 \cdot \sum_{i=1}^{N_m} (\tilde{A}_i^{(+)} - A_i(v_m, a, \{a_i\})) \cdot \sum_{k=1}^{N_m} a_k \frac{\partial F_{i,k}(v_m, a)}{\partial v_m}, \tag{29}$$

and, $$\frac{\partial E}{\partial a} = -2 \cdot \sum_{i=1}^{N_m} (\tilde{A}_i^{(+)} - A_i(v_m, a, \{a_i\})) \cdot \sum_{k=1}^{N_m} a_k \frac{\partial F_{i,k}(v_m, a)}{\partial a}. \tag{30}$$

The derivative in Eq. 29 of the objective function requires differentiation of $F_{i,l}$ with respect to $v_m$. According to Eq. 17, this differentiation requires the derivative of the speed-dependent polarization function, i.e., $$\frac{\partial F_{i,1}(v_m, a)}{\partial v_m} = \frac{a^2}{r_o^2} \frac{\partial f_{i,1}(v_m)}{\partial v_m} + \frac{(r_o - a)^2}{2r_o^2} \sum_{k=1}^{n} w_k \frac{\partial f_{i,1}(v_m \cdot \xi_k)}{\partial v_m}. \tag{31}$$

In taking the derivatives in Eq. 31, the order of integration and differentiation is interchanged and a compact notation for the speed-dependent polarization functions is introduced as follows:

$$f_{i,l}(\theta_m \cdot \xi) \equiv f(v_m \xi, T_{1,l}, l_a, l_p, W_i) \tag{32}$$

which can be obtained from Eqs. 8a and 8b by making the substitution, $v = v_m \cdot \xi$. Because the inversion depends critically on the accuracy of these derivatives, it is useful to display the detailed results. The derivatives in the summation of Eq. 31 are given by, $$\frac{\partial f_{i,1}(v_m \cdot \xi)}{\partial v_m} = \frac{\xi \cdot W_i}{l_a} - \tag{33}$$

$$\left[ \frac{(l_p + v_m \cdot \xi \cdot T_{i,l})}{v_m \cdot l_a} \cdot \exp\left(-\frac{l_p}{v_m \cdot \xi \cdot T_{i,l}}\right) + \frac{\xi \cdot W_i}{l_a} \right] \cdot \left(1 - \exp\left(-\frac{W_i}{T_{i,l}}\right)\right),$$

when $\xi < l_a/(v_m \cdot W_i)$, and $$\frac{\partial f_{i,j}(v_m \cdot \xi)}{\partial v_m} = \tag{34}$$

$$-\left(1 - \exp\left(-\frac{l_o}{v_m \cdot \xi \cdot T_{i,l}}\right)\right) \cdot \frac{(l_p + v_m \cdot \xi \cdot T_{i,l})}{v_m \cdot l_a} \cdot \exp\left(-\frac{l_p}{v_m \cdot \xi \cdot T_{i,l}}\right) +$$

$$\frac{1}{v_m} \exp\left(-\frac{l_a + l_p}{v_m \cdot \xi \cdot T_{i,l}}\right)$$

when $\xi \geq l_a/(v_m \cdot W_i)$.

Note that the partial derivatives for the first term on the right hand side of Eq. 31 can be obtained from Eqs. 33 and 34 by setting $\xi = 1$. The partial derivative of $F_{i,l}$ with respect to $a$ in Eq. 30 is straightforward and can readily be obtained by differentiation of Eq. 17.

Inversion Method No. 2

The approach described in the previous section fits the phase corrected data to the relaxation model. An alternative approach described below simultaneously fits the two channel data to the forward model. An error or objective function, similar to that of Eq. 27, may be defined as:

$$E(v_m, a, \{a_{l,r}\}, \{a_{l,q}\}) = \sum_{i=1}^{N_m} (\tilde{A}_{i,r} - A_{i,r}(v_m, a, \{a_{l,r}\}))^2 + \tag{35}$$

$$\sum_{i=1}^{N_m} (\tilde{A}_{i,q} - A_{i,q}(v_m, a, \{a_{l,q}\}))^2 + \gamma \sum_{i=1}^{N_m} a_i^2,$$

where $$A_{i,r} = A_i \cos \phi, \tag{36a}$$

$$A_{i,q} = A_i \sin \phi, \tag{36b}$$

$$a_{i,r} = a_1 \cos \phi, \tag{36c}$$

and $$a_{1,q} = a_1 \sin \phi. \tag{36d}$$

The objective function of Eq. 35 may be minimized with respect to $v_m$, a, and the two sets of amplitudes $\{a_{l,r}\}$ and $\{a_{l,q}\}$. The amplitudes in the $T_1$ distribution may be computed directly from the two sets of amplitudes using the equation, $$a_i = \sqrt{a_{i,r}^2 + a_{i,q}^2}. \tag{37}$$

The signal phase can also be estimated from these amplitudes using the equation, $$\hat{\phi} = \arctan\left(\frac{\sum_{i=1}^{N_c} a_{l,q}}{\sum_{i=1}^{N_c} a_{l,r}}\right), \tag{38}$$

where $N_c$ is the number of components used to approximate the $T_1$ distribution. Again, the minimization of the objective function in Eq. 35 may be accomplished with any of a number of commercially available programs (e.g., DLCONG) and the partial derivatives discussed in the previous section.

Numerical Simulations

Embodiments of the invention can accurately estimate the flow speed and $T_1$ values (either a distribution or an average of the $T_1$ values of the fluid) in a flowing fluid. The following describes several computer simulation experiments that demonstrate the accuracy with which $v_m$ and $T_1$ can be estimated using embodiments of the invention. The simulations were performed for an NMR sensor (as shown in FIG. 2) with $l_a$=0.5 in., $l_p$=10.0 in. and $r_o$=0.1 in. There were 35 wait times in the variable wait time suite ranging from 0.001 s to 0.72 s. The average flow speeds used in the simulations were 2.5, 5.0, 10.0, 15.0, 20.0, 25.0, 30.0, 35.0 and 40.0 in/s.

Figure 5:
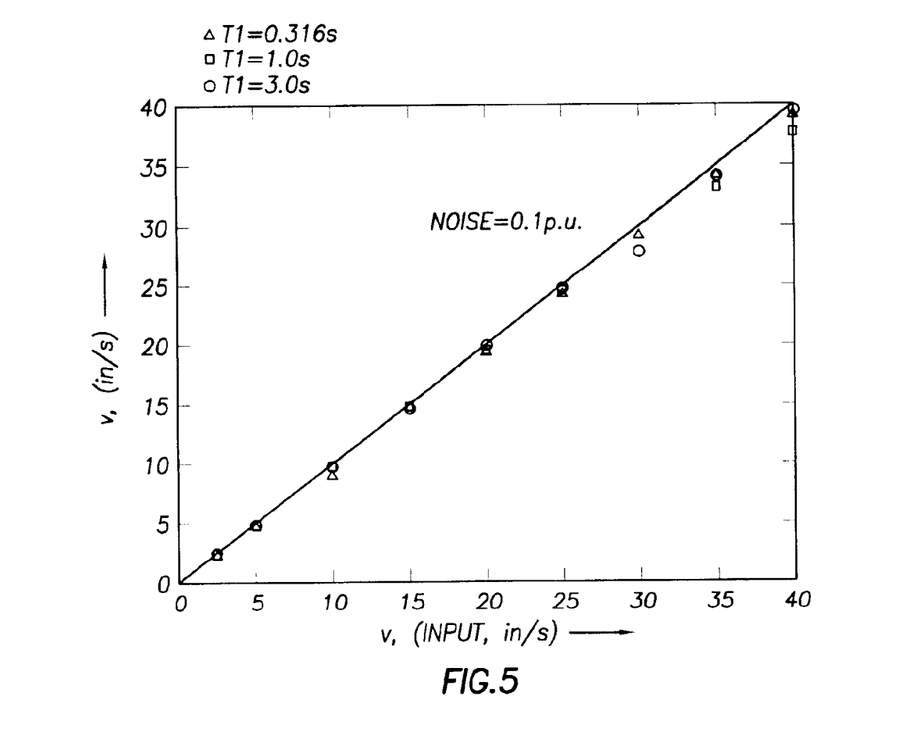
FIG. 5 shows computed flow speeds versus input flow speeds in a simulation according to one embodiment of the invention.

FIG. 5 shows a comparison of the average fluid velocity ($=v_m/2$) versus the estimated average fluid velocity. The simulation was performed assuming an rms noise amplitude of 0.1 p.u. This is a relatively high signal-to-noise ratio considering that the signal amplitude is 100 p.u. when measured on a fully polarized stationary fluid. The simulation shown in FIG. 5 was performed for three different fluids having a range of $T_1$ values. The $T_1$ distributions used in the simulations were single valued (i.e., Dirac delta functions). Note that there is good agreement for all three fluids between the estimated average flow speed (y-axis) and the input values (x-axis) used in the simulation. There is some loss of accuracy at the higher average flow speeds (e.g., above about 30 in/s). However, the estimates are reasonably good considering the high flow speeds.

Figure 6:
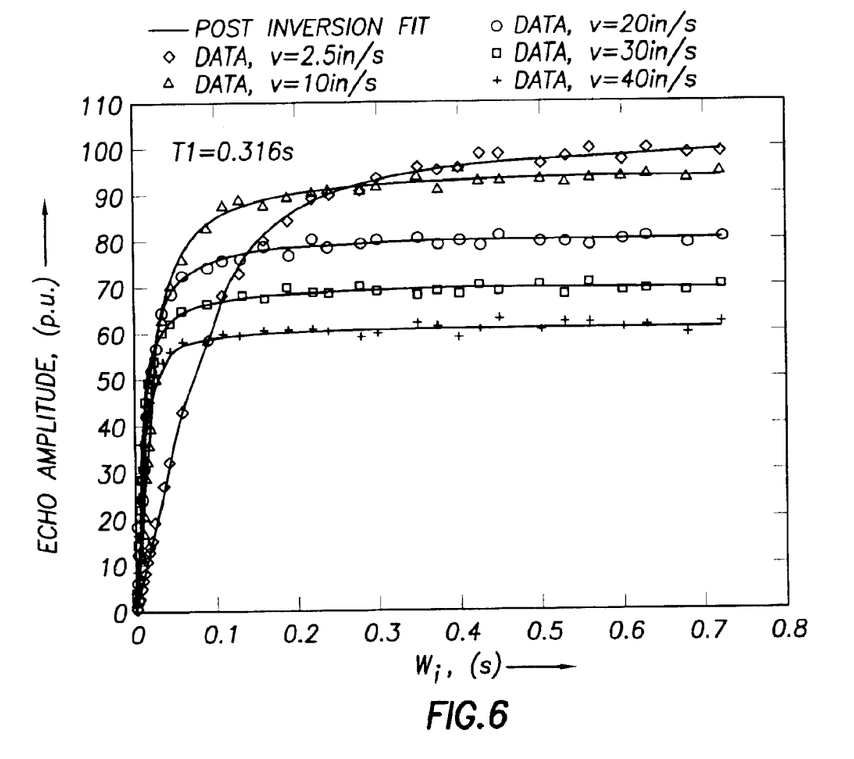
FIG. 6 shows the fitting of signal magnitudes to a suite of data with variable wait times for various flowing speeds according to one embodiment of the invention.

FIG. 6 shows the variable wait time data suites as a function of flow speed, for a fluid having $T_1$=0.316 s, and the post-inversion fits of the forward model to these data. Note that in FIG. 6 the measured echo amplitudes decrease significantly with increasing flow speed due to incomplete polarization. This may account for the loss of accuracy in the flow speed estimates in FIG. 5 at higher flow speeds. This effect is exacerbated for fluids with long $T_1$'s.

Figure 7:
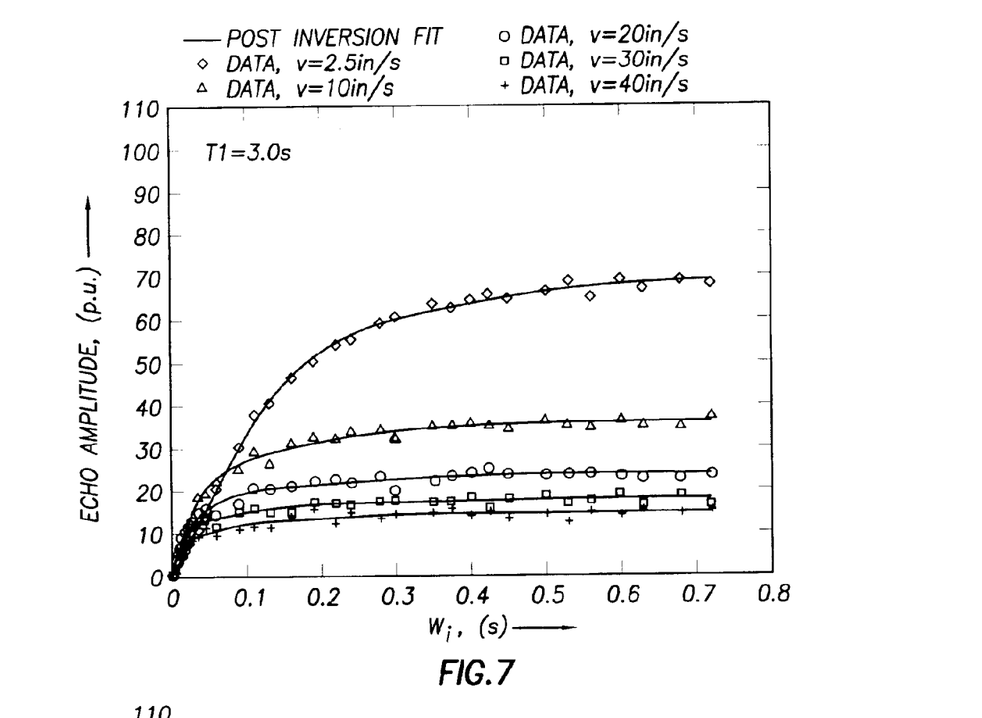
FIG. 7 shows the fitting of signal magnitudes to a suite of data with variable wait times for various flowing speeds according to one embodiment of the invention.

FIG. 7 shows the variable wait time data and the post-inversion fit for a fluid having $T_1$=3 s at various flow speeds.

The quality of the fit is assessed by a dimensionless chi-squared "goodness of fit" parameter defined as, $$\chi^2 = \frac{1}{N_w \cdot \sigma^2} \sum_{i=1}^{N_w} \left(\tilde{A}_i^{(+)} - A_i(v_m, a, \{a_l\})\right)^2. \tag{39}$$

For a perfect fit, $\chi^2 \approx 1$, to within noise errors.

Note the significant reduction in the echo amplitudes with increasing flow speed. This translates into a significant reduction in the measurement signal-to-noise ratios. Another important feature of the data in FIG. 7 is the compression of the data (i.e., the curves are closer together) as the flow speed increases. Thus, the relative sensitivity to flow speed of measurements made at high flow speed is reduced. Both of these effects, reduced signal-to-noise ratio and reduced sensitivity, mean that it is more difficult to accurately invert a variable wait time data suite at higher flow speeds.

Figure 8:
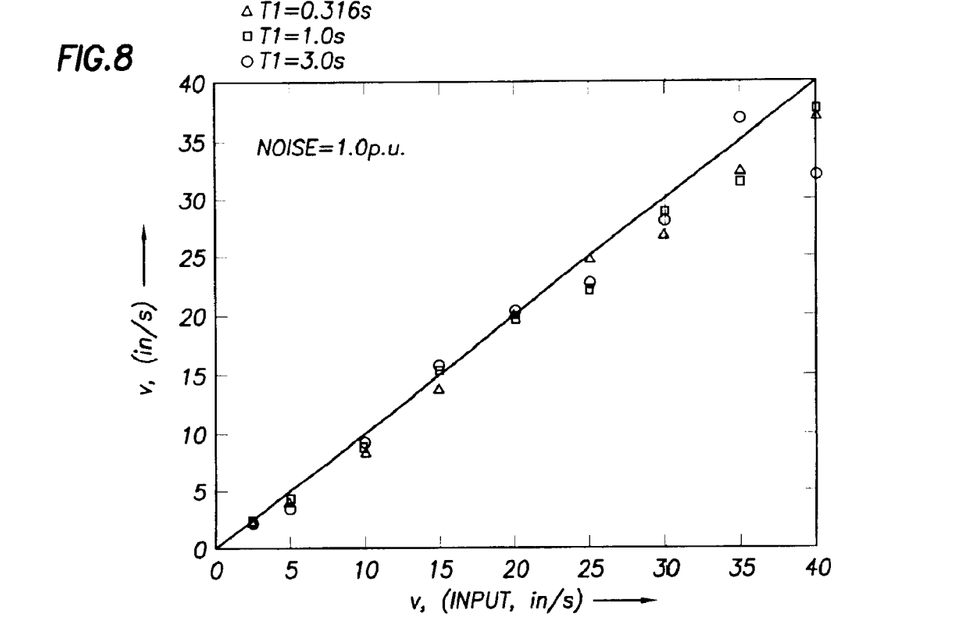
FIG. 8 shows computed flow speeds versus input flow speeds, for fluids with different $T_1$s, in a simulation according to one embodiment of the invention.
Figure 9:
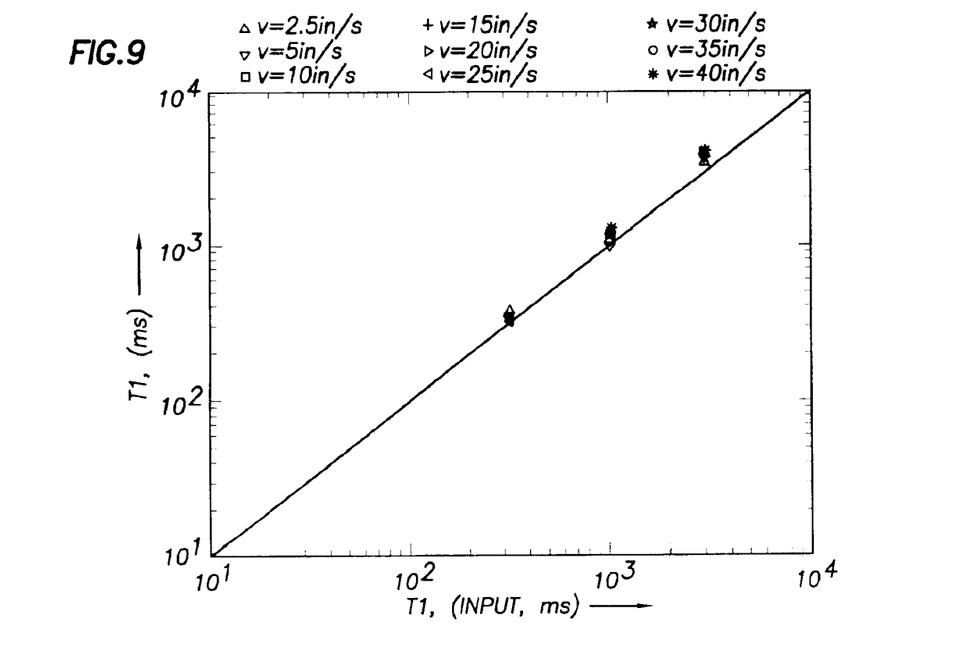
FIG. 9 shows computed $T_1$ versus input $T_1$ for various flow speeds in a simulation according to one embodiment of the invention.

FIG. 8 shows the results of the same simulation as in FIG. 5, but with an rms noise of 1.0 p.u. instead of 0.1 p.u. A comparison of FIGS. 5 and 8 reveals that the quality of the flow speed estimation is significantly degraded by a tenfold reduction in the signal-to-noise ratio. This clearly shows the importance of having high signal-to-noise ratio measurements.

For fluids with broad $T_1$ distributions, the geometric mean of the distributions or other moments of the distribution can be used to monitor and characterize the fluids in the flowline.

Estimation of Fluid Viscosity from the Measurements

As noted above, some embodiments of the invention relate to methods for estimating fluid viscosity from NMR measurements of a flowing fluid. Once the flow speed of the fluid is determined from a suite of NMR measurements having variable wait times according to methods described above, the viscosity of the fluid can also be estimated according to methods described in the following sections. Two methods will be described for estimating fluid viscosity ($\eta$) using the variable wait time measurements made on flowing fluids in the flowline. One of ordinary skill in the art would appreciate that these two approaches are for illustration only, and other methods may be used without departing from the scope of the invention.

The first method computes an estimate of the viscosity ($\eta$) using the average flow speed (v) estimated from the NMR measurements and the measured pressure drop, $\Delta P$, across a length L of the flowline. The pressure drop, $\Delta P$, may be obtained from pressure sensors equipped on the NMR sensor or the formation testing tool. The computation of fluid viscosity from the flow speed (v) and the pressure drop ($\Delta P$) may be accomplished according to the well-known fluid mechanics formula (See e.g., Victor L. Streeter et al., *Fluid Mechanics*, 5$^{th}$ Edition. p. 244, McGraw-Hill, NY.):

$$\eta = \frac{\Delta P \cdot r_o^2}{8 \cdot v \cdot L}, \tag{40}$$

where the average speed v of the fluid is equal to $v_m/2$. Because L and $r_o$ are defined by the apparatus, Eq. 40 may be converted to a more general form, $$\eta = K \cdot \frac{\Delta P}{v}, \quad (41)$$

where the proportionality constant K may be determined empirically from measurements made on fluids with known viscosities measured at different speeds with known pressure gradients. Using v, η and an independent measure of the mass density of the fluid, it is possible to compute the Reynolds number, R, from Eq. 3. The computation in Eq. 40 or 41 is valid for any viscous fluid and is not restricted to crude oil or brine.

The second approach for estimating crude oil viscosity is to use the geometric or logarithmic mean of the $T_1$ distribution. The logarithmic mean of the $T_1$ distribution is related to the oil viscosity by a known correlation (See e.g., Freedman et al., "A New NMR Method of Fluid Characterization in Reservoir Rocks: Experimental Confirmation and Simulation Results," SPE Journal, December 2001, 452–464), $$\eta_o = \frac{kT}{T_{1,LM} \cdot f(GOR)}, \quad (42)$$

where $\eta_o$ is the oil viscosity in centipoise, k is an empirically determined constant for crude oils, T is the temperature in Kelvin, $T_{1,LM}$ is the logarithmic mean of the oil $T_1$ distribution and $f(GOR)$ is an empirically determined function of the solution gas-oil ratio (GOR). The GOR in Eq. 42 may be determined from other measurements in the flowline or might be known from local or prior knowledge of the reservoir fluid properties.

The computed $T_1$ distribution or the viscosity of the flowing fluid computed from Eq. 40, 41, or 42 can be used to monitor changes in the contamination of the fluid in the flowline. This application will be described in the following sections.

Figure 10:
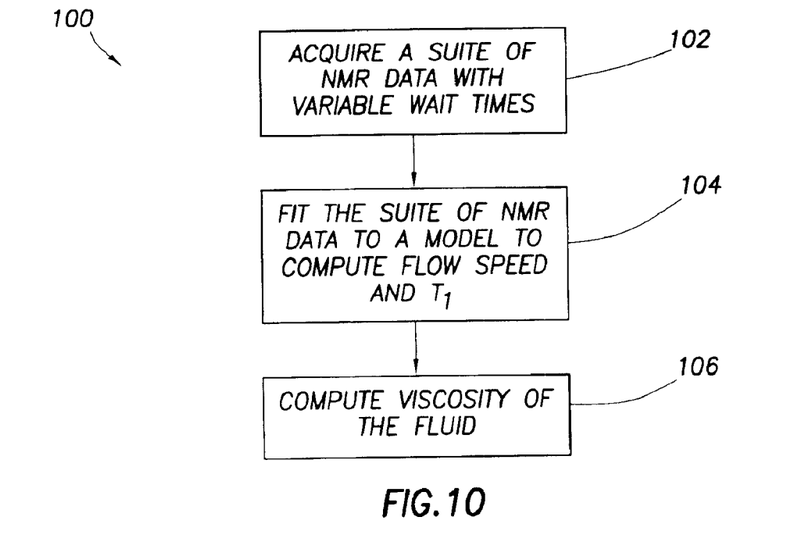
FIG. 10 shows a flow chart of a method for determining the flow speed and properties of a flowing fluid according to one embodiment of the invention.

FIG. 10 illustrates a method 100 in accordance with embodiments of the invention. In accordance with this method, a suite of NMR data are acquired with variable wait times (step 102). The pulse sequences for the data acquisition may include a spoiling pulse, a wait time, and an acquisition pulse sequence, as shown in FIGS. 3A and 3B. The acquisition pulse sequence may include a simple 90-degree excitation pulse, a spin-echo pulse (90-delay-180), a Carl-Purcell-Meiboom-Gill (CPMG) pulse, or any variant of the spin-echo or CPMG pulse. A single spin-echo pulse is shown in FIG. 3B for illustration. The 90-degree and the 180-degree pulses shown may be replaced with other pulses (e.g., composite pulses) without departing from the scope of the invention.

As noted above, in addition to the variable wait time pulse sequence shown in FIGS. 3A and 3B, embodiments of the invention may also use other $T_1$ investigation pulse sequences. For example, an inversion-recovery pulse sequence or a saturation-recovery pulse sequence may be used instead. If a saturation-recovery pulse sequence is used, the model fitting process is similar to that using the spoiling pulse sequence. However, if an inversion-recovery pulse sequence is used, then the spin polarization function of Eq. 1 would be modified.

Once the suite of variable wait time NMR measurements are acquired, they may be fit to a forward model using either of the inversion methods discussed above (step 104). The inversion process produces the flow speed (v) and the $T_1$ values of the flowing fluid. The $T_1$ values thus obtained may be a $T_1$ distribution or a logarithmic mean of the $T_1$ distribution.

The flow speed (v) and/or the $T_1$ values obtained from fitting the NMR data to a flow model may be used to compute the viscosity of the flowing fluid (step 106). As noted above, the estimated flow speed (v) together with an independently measured pressure drop (ΔP) across the length L of the NMR sensor may be used to compute the fluid viscosity (θ) according to Eq. 40 or 41. Similarly, the estimated $T_1$ values or its logarithmic mean may be used together with an independently determined GOR function, $f(GOR)$, to compute the fluid viscosity (η), as shown in Eq. 42. However, any variations of these approaches may be used.

As noted above, embodiments of the invention may be used to monitor fluid contamination as they are withdrawn from the formation. With the ability to compute the $T_1$ and viscosity of the flowing fluid according to methods shown in FIG. 10, it becomes possible to monitor the purity of the formation fluids as they are drawn into the formation fluid testing tool.

Figure 11:
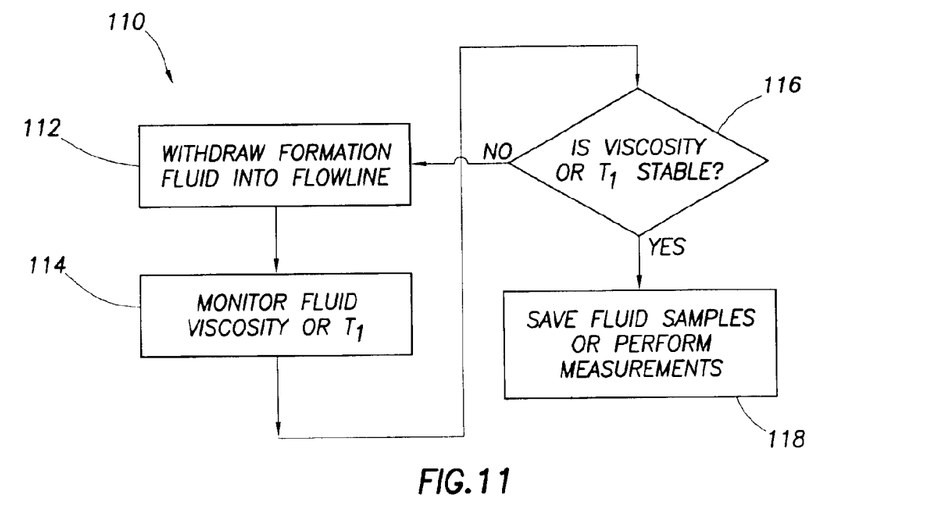
FIG. 11 shows a flow chart of a method for monitoring contamination in a flowing fluid in a formation fluid testing tool in accordance with one embodiment of the invention.

FIG. 11 shows a method 110 for such monitoring in accordance with a method of the invention. According to this method, formation fluids are withdrawn into the testing tool (step 112) and the viscosity or $T_1$ values of the fluids are monitored (step 114). Because the early portion of the withdrawn fluids are likely contaminated with mud filtrates, their properties (e.g., viscosity and $T_1$ values) are likely different from un-contaminated formation fluids. As the flow of the formation fluids continues, the level of the mud filtrate contamination will gradually decrease. Therefore, by monitoring the viscosity or the $T_1$ values of the flowing fluids, it is possible to discern when the mud filtrate contamination diminishes to an insignificant level, for example by monitoring the viscosity or $T_1$ values approaching a steady state value that reflects the properties of the pure formation fluids.

By querying whether the viscosity or the $T_1$ values reach a stable value (step 116), a decision can be made whether to continue the withdrawal of the formation fluids. For example, if the viscosity or $T_1$ values has not stabilized, the withdrawal process and the monitoring will be continued. If the viscosity or the $T_1$ values stabilize, then the withdrawn fluid samples may be saved for later analysis, or a downhole measurement may be performed in situ (step 118).

Various NMR measurements have been performed downhole. For example, U.S. Pat. No. 6,229,308 issued to Freedman and U.S. Pat. No. 6,462,541 B1 issued to Venkataramanan et al. disclose NMR measurements under downhole conditions. These measurements can provide $T_2$ (transverse relaxation times) distribution, D (diffusion) distributions of the formation fluids, $T_2$-D maps, fluid typing, and fluid viscosity (η).

Method 110 shown in FIG. 11 is functionally equivalent to many monitoring techniques currently used to monitor contamination in fluids withdrawn by a formation fluid testing tool. Other methods may monitor, for example, color, optical density, or GOR of the fluids. Thus, method 110 shown in FIG. 11 provides an alternative to these existing methods.

The methods as shown in FIGS. 10 and 11 may be implemented as computer programs and stored on a computer or a processor used with well logging, for example the processor or circuitry included in the electronic module 11 shown in FIG. 1.

Advantages of the invention include the following. Embodiments of the invention provide convenient methods for estimating flow speed, $T_1$ values, and viscosity of a flowing fluid. Methods of the invention may be used on a formation fluid testing tool or in any other type of apparatus and application where one needs to monitor fluid flow. If used on a formation testing tool methods of the invention may be used to monitor contamination of the formation fluids as they are removed from the formation. These methods ensure that formation fluids substantially free from contamination are removed for analysis. By providing methods for monitoring contamination in formation fluids while they are being withdrawn, methods of the invention can alleviate problems associated with contamination in formation fluid analysis. In addition, methods of the invention also provide NMR measurements downhole, after the monitoring indicates that contamination is insignificant. Being able to measure the fluid properties under conditions close to reservoir conditions can provide fluid properties that are representative of the in situ fluid properties.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for determining a property of a flowing fluid by nuclear magnetic resonance, comprising:

applying a static magnetic field to the flowing fluid;

acquiring a suite of nuclear magnetic resonance measurements on the flowing fluid using a pulse sequence comprising a spoiling pulse, a wait time, and an acquisition pulse sequence, wherein the suite of nuclear magnetic measurements have different values for the wait time; and fitting the suite of nuclear magnetic resonance measurements to a forward model for responses of the flowing fluid to derive a parameter selected from a flow speed, longitudinal relaxation times of the flowing fluid, and a combination thereof.

2. The method of claim 1, wherein the acquisition pulse sequence comprises one selected from a spin-echo pulse sequence and a single pulse.

3. The method of claim 1, wherein the fitting is performed by inversion of the forward model.

4. The method of claim 1, further comprising estimating a viscosity of the flowing fluid based on the derived flow speed and a pressure drop across a selected length of a pipe in which the flowing fluid travels.

5. The method of claim 4, wherein the estimating is according to one selected from $$\eta = \frac{\Delta P \cdot r_o^2}{8 \cdot v \cdot L} \text{ and } \eta = K \cdot \frac{\Delta P}{v},$$

where $\eta$ is the viscosity, $v$ is an average speed of the flowing fluid, $L$ is the selected length of the pipe, $\Delta P$ is the pressure drop over the selected length of the pipe, and $r_o$ is a radius of the pipe, and $K$ is an experimentally determined constant.

6. The method of claim 1, further comprising estimating a viscosity of the flowing fluid based on the derived longitudinal relaxation times and a gas-oil ratio of the flowing fluid.

7. The method of claim 6, wherein the estimating is according to:

$$\eta_o = \frac{kT}{T_{1,LM} \cdot f(GOR)}$$

where $\eta_o$ is the viscosity, $k$ is an empirically determined constant for the flowing fluid, $T$ is a temperature in Kelvin, $T_{1,LM}$ is a logarithmic mean of the longitudinal relaxation times of the flowing fluid, and $f(GOR)$ is an empirically determined function of the gas-oil ratio.

8. A method for determining a property of a flowing fluid by nuclear magnetic resonance, comprising:

applying a static magnetic field to the flowing fluid;

acquiring a suite of nuclear magnetic resonance measurements on the flowing fluid using a pulse sequence comprising a longitudinal relaxation investigation pulse sequence and an acquisition pulse sequence, wherein the suite of nuclear magnetic measurements have different values for a delay time within the longitudinal relaxation investigation pulse; and fitting the suite of nuclear magnetic resonance measurements to a forward model for responses of the flowing fluid to derive a parameter selected from a flow speed, longitudinal relaxation times of the flowing fluid, and a combination thereof.

9. The method of claim 8, wherein the longitudinal-relaxation-investigation pulse comprises one selected from a inversion-recovery pulse sequence and a saturation-recovery pulse sequence.

10. The method of claim 8, wherein the acquisition pulse sequence comprises one selected from a spin-echo pulse sequence and a single pulse.

11. The method of claim 8, wherein the fitting is performed by inversion of the forward model.

12. The method of claim 8, further comprising estimating a viscosity of the flowing fluid based on the derived flow speed and a pressure drop across a selected length of a pipe in which the flowing fluid travels.

13. The method of claim 12, wherein the estimating is according to one selected from $$\eta = \frac{\Delta P \cdot r_o^2}{8 \cdot v \cdot L} \text{ and } \eta = K \cdot \frac{\Delta P}{v},$$

where $\eta$ is the viscosity, $v$ is an average speed of the flowing fluid, $L$ is the selected length of the pipe, $\Delta P$ is the pressure drop over the selected length of the pipe, and $r_o$ is a radius of the pipe, and $K$ is an experimentally determined constant.

14. The method of claim 8, further comprising estimating a viscosity of the flowing fluid based on the derived longitudinal relaxation times and a gas-oil ratio of the flowing fluid.

15. The method of claim 14, wherein the estimating is according to:

$$\eta_o = \frac{kT}{T_{1,LM} \cdot f(GOR)}$$

where $\eta_o$ is the viscosity, $k$ is an empirically determined constant for the flowing fluid, $T$ is a temperature in Kelvin, $T_{1,LM}$ is a logarithmic mean of the longitudinal relaxation times of the flowing fluid, and $f(GOR)$ is an empirically determined function of the gas-oil ratio.

16. A method for monitoring contamination in a flowing fluid being withdrawn into a formation fluid testing tool using nuclear magnetic resonance, comprising:

applying a static magnetic field to the flowing fluid;

acquiring a suite of nuclear magnetic resonance measurements of the flowing fluid using a pulse sequence comprising a spoiling pulse, a wait time, and an acquisition pulse sequence, wherein the suite of nuclear magnetic measurements have different values for the wait time;

fitting the suite of nuclear magnetic resonance measurements to a forward model for responses of the flowing fluid to derive a property of the flowing fluid; and monitoring a level of contamination in the flowing fluid based on the derived property of the flowing fluid.

17. The method of claim 16, wherein the property of the flowing fluid comprises one selected from a distribution of longitudinal relaxation times, a logarithmic mean of longitudinal relaxation times, and a combination thereof.

18. The method of claim 16, wherein the property of the flowing fluid is a viscosity.

19. A nuclear magnetic resonance apparatus, comprising:

a flow pipe including a prepolarization section and an investigation section, wherein the prepolarization section is upstream of the investigation section;

a magnet disposed around the flow pipe for creating a static magnetic field covering the prepolarization section and the investigation section;

an antenna disposed around the flow pipe at the investigation section for generating an oscillating magnetic field having a magnetic dipole substantially perpendicular to a magnetic dipole of the static magnetic field, and for receiving a nuclear magnetic resonance signal; and a circuitry for controlling generation of the oscillating magnetic field and reception of the nuclear magnetic resonance signal by the antenna, wherein the circuitry includes a program having instructions for acquiring a suite of nuclear magnetic resonance measurements of a flowing fluid using a pulse sequence comprising a spoiling pulse, a wait time, and an acquisition pulse sequence.

20. The apparatus of claim 19, wherein the acquisition pulse sequence comprises one selected from a spin-echo pulse sequence and a single pulse.

21. The apparatus of claim 19, wherein the program further comprises instructions for fitting the suite of nuclear magnetic resonance measurements to a forward model for responses of a flowing fluid to derive a parameter selected from a flow speed, longitudinal relaxation times of the flowing fluid, and a combination thereof.

22. The apparatus of claim 21, wherein the fitting is performed by inversion of the forward model.

23. The apparatus of claim 21, wherein the program further comprising instructions for estimating a viscosity of the flowing fluid based on the derived flow speed or the derived longitudinal relaxation times.

24. A nuclear magnetic resonance apparatus, comprising:

a flow pipe including a prepolarization section and an investigation section, wherein the prepolarization section is upstream of the investigation section;

a magnet disposed around the flow pipe for creating a static magnetic field covering the prepolarization section and the investigation section;

an antenna disposed around the flow pipe at the investigation section for generating an oscillating magnetic field having a magnetic dipole substantially perpendicular to a magnetic dipole of the static magnetic field, and for receiving a nuclear magnetic resonance signal; and a circuitry for controlling generation of the oscillating magnetic field and reception of the nuclear magnetic resonance signal by the antenna, wherein the circuitry includes a program having instructions for acquiring a suite of nuclear magnetic resonance measurements of a flowing fluid using a pulse sequence comprising a longitudinal relaxation investigation pulse sequence and an acquisition pulse sequence, wherein the suite of nuclear magnetic measurements have different values for a delay time within the longitudinal relaxation investigation pulse.

25. The apparatus of claim 24, wherein the acquisition pulse sequence comprises one selected from a spin-echo pulse sequence and a single pulse.

26. The apparatus of claim 24, wherein the program further comprises instructions for fitting the suite of nuclear magnetic resonance measurements to a forward model for responses of a flowing fluid to derive a parameter selected from a flow speed, longitudinal relaxation times of the flowing fluid, and a combination thereof.

27. The apparatus of claim 26, wherein the fitting is performed by inversion of the forward model.

28. The apparatus of claim 26, wherein the program further comprising instructions for estimating a viscosity of the flowing fluid based on the derived flow speed or the derived longitudinal relaxation times.

* * * * *